United States Patent
Mandal et al.

(10) Patent No.: US 11,723,866 B2
(45) Date of Patent: *Aug. 15, 2023

(54) PHARMACEUTICAL SOLUTION OF AMLODIPINE

(71) Applicant: LIQMEDS WORLDWIDE LIMITED, Haynes (GB)

(72) Inventors: Jayanta Kumar Mandal, Ahmedabad (IN); Malay Patel, Ahmedabad (IN); Swati Nagar, Amreli (IN); Michael Paul DeHart, Winterville, NC (US)

(73) Assignee: LIQMEDS WORLDWIDE LIMITED, Hayes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/840,829

(22) Filed: Jun. 15, 2022

(65) Prior Publication Data

US 2022/0313605 A1 Oct. 6, 2022

Related U.S. Application Data

(63) Continuation of application No. 17/575,693, filed on Jan. 14, 2022, now Pat. No. 11,458,095, which is a continuation of application No. 17/183,553, filed on Feb. 24, 2021, now Pat. No. 11,253,474.

(60) Provisional application No. 63/144,021, filed on Feb. 1, 2021.

(51) Int. Cl.
| | | |
|---|---|---|
| A61K 9/08 | (2006.01) | |
| A61K 47/26 | (2006.01) | |
| A61K 47/10 | (2017.01) | |
| A61K 31/4418 | (2006.01) | |

(52) U.S. Cl.
CPC ............ *A61K 9/08* (2013.01); *A61K 31/4418* (2013.01); *A61K 47/10* (2013.01); *A61K 47/26* (2013.01)

(58) Field of Classification Search
CPC ...... A61K 9/08; A61K 31/4418; A61K 47/10; A61K 47/26
See application file for complete search history.

(56) References Cited

U.S. PATENT DOCUMENTS

| 4,879,303 | A | 11/1989 | Davison et al. |
| 7,108,885 | B2 | 9/2006 | Serpelloni |
| 10,695,329 | B2 | 6/2020 | Brauer et al. |
| 2011/0294860 | A1 | 12/2011 | Tatsumi et al. |
| 2018/0303811 | A1 | 10/2018 | Mandal et al. |
| 2019/0365732 | A1 | 12/2019 | Ritter |

FOREIGN PATENT DOCUMENTS

| GB | 2166637 A | 5/1986 |
| JP | 2009-256216 A | 11/2009 |

OTHER PUBLICATIONS

Berge et al., Pharmaceutical Salts, J. Pharm. Science (1977) 66(1): 1-19 ("Berge").
Handbook of Pharmaceutical Excipients, Sixth Edition (2009), Rowe et al. Eds. ("Handbook").
Katerzia® (amlodipine) oral suspension, for oral use, prescribing information as of Jul. 8, 2019 ("Katerzia® Label").
Murakami et al., Application of liquid chromatography-two-dimensional nuclear magnetic resonance spectroscopy using pre-concentration column trapping and liquid chromatography—mass spectrometry for the identification of degradation products in stressed commercial amlodipine maleate tablets, J. Chromatog. A (2008) 1181(1-2): 67-76 ("Murakami").
Nahata et al., Stability of Amlodipine Besylate in Two Liquid Dosage Forms, J Am. Pharm Assoc. (1999) 39: 375-377 ("Nahata").
Norvasc® (amlodipine besylate) tablets for oral administration prescribing information, as of Oct. 30, 2017 ("Norvasc® Label").
Ragno et al., Photodegradation monitoring of amlodipine by derivative spectrophotometry, J. Pharm. Biomed. Anal. (2002)27(1): 19-24 ("Ragno").
Rapolu et al., Isolation and characterization of a novel acid degradation impurity of Amlodipine Besylate using Q-TOF, NMR, IR and single crystal X-ray, J. Pharm. Biomed. Anal. (2014) 99: 59-66 ("Rapolu").
Stopher et al., The Metabolism and Pharmacokinetics of Amlodipine in Humans and Animals, J. Cardiovasc Pharmacol (1988) 12(Suppl. 7): S55-S59 ("Stopher").
Friciu et al., Stability of Extemporaneously Compounded Amlodipine Besylate Oral Suspensions, The Canadian Journal of Hospital Pharmacy (2016) 69(4): 327-329.
Van der Vossen et al., Design and stability study of an oral solution of amlodipine besylate for pediatric patients, European Journal of Pharmaceutical Sciences (2016) 92: 220-223.

*Primary Examiner* — Robert A Wax
*Assistant Examiner* — Quanglong N Truong
(74) *Attorney, Agent, or Firm* — Merchant & Gould P.C.; Daniel R. Evans

(57) ABSTRACT

Disclosed herein is a liquid pharmaceutical formulation substantially free of water, comprising: (i) amlodipine or a pharmaceutically acceptable salt thereof, (ii) at least one pharmaceutically acceptable excipient, and (iii) a sufficient amount of a vehicle comprising glycerin. Also disclosed herein is a liquid pharmaceutical formulation substantially free of water and ethanol, comprising: (i) amlodipine or a pharmaceutically acceptable salt thereof, (ii) at least one pharmaceutically acceptable excipient, and (iii) a sufficient amount of a vehicle comprising glycerin.

30 Claims, No Drawings

PHARMACEUTICAL SOLUTION OF AMLODIPINE

RELATED APPLICATIONS

This application is a continuation of U.S. patent application Ser. No. 17/575,693, filed on Jan. 14, 2022, now U.S. Pat. No. 11,458,095, which is a continuation of U.S. patent application Ser. No. 17/183,553, filed on Feb. 24, 2021, now U.S. Pat. No. 11,253,474, which claims priority to U.S. Provisional Patent Application No. 63/144,021, filed on Feb. 1, 2021.

FIELD

The disclosure relates to an oral pharmaceutical solution comprising amlodipine or a pharmaceutically acceptable salt thereof.

BACKGROUND

High blood pressure or hypertension is a common condition in which the long-term force of the blood against artery walls is high enough that it may eventually cause health problems, such as heart disease. Blood pressure is determined both by the amount of blood pumped by the heart and the amount of resistance to blood flow in arteries. Pumping blood through narrowed arteries may result in high blood pressure or even hypertension. Although a hypertensive patient may be asymptomatic, long-lasting vascular and heart damage may occur. Uncontrolled high blood pressure increases the risk of serious health problems, including heart attack and stroke. Hypertension generally develops over many years, and it affects nearly everyone eventually. Fortunately, hypertension may be detected easily, and once detected, one can work with your doctor to control it.

Many blood pressure medications, known as antihypertensives, are available by prescription to lower high blood pressure or hypertension. There are a variety of classes of high blood pressure medications and they include a number of different drugs and can be broadly classified by the following classes: Diuretics, Beta-blockers, ACE inhibitors, Angiotensin II receptor blockers, Calcium channel blockers, Alpha blockers, Alpha-2 Receptor Agonists, Combined alpha and beta-blockers, Central agonists, Peripheral adrenergic inhibitors, and Vasodilators.

Amlodipine is an angioselective calcium channel blocker and inhibits the movement of calcium ions into vascular smooth muscle cells and cardiac muscle cells which inhibits the contraction of cardiac muscle and vascular smooth muscle cells. Amlodipine is available in different salts like amlodipine besylate, amlodipine maleate, amlodipine orotate, amlodipine adipate, amlodipine camsylate, amlodipine nicotinate, and many more. Amlodipine is referred to by the chemical name 3-ethyl-5-methyl (±)-2-[(2-aminoethoxy)methyl]-4-(2-chlorophenyl)-1,4-dihydro-6-methyl-3,5-pyridinedicarboxylate with a CAS No. of 88150-42-9, and with the following chemical structure.

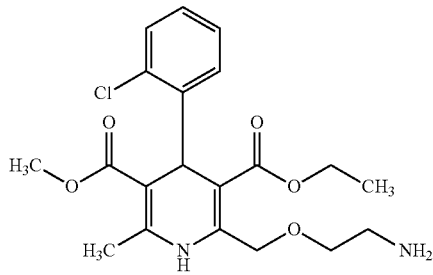 [SMILES: CCOC(=O)C1=C(COCCN)NC(C)=C(C(=O)OC)C1c1ccccc1Cl]

Amlodipine besylate is a white crystalline powder with a molecular weight of 567.1, is slightly soluble in water, and sparingly soluble in ethanol.

Amlodipine is commercially available as NORVASC® (amlodipine besylate) Tablets in strengths of tablets equivalent to 2.5, 5, and 10 mg of amlodipine for oral administration. In addition to the amlodipine besylate, each tablet contains the following inactive ingredients: microcrystalline cellulose, dibasic calcium phosphate anhydrous, sodium starch glycolate, and magnesium stearate. The 10-mg dosage strength for NORVASC® is the reference listed drug (or reference product).

Amlodipine undergoes extensive metabolism and none of the metabolites have significant calcium antagonist activity relative to amlodipine. See, e.g., Stopher at S56. One of the amlodipine metabolites, known as Amlodipine Related Substance A (or "Impurity A" (alternatively referred to as Amlodipine Besylate EP Impurity D" or "Dehydro Amlodipine") having a CAS No. of 113994-41-5), may form from amlodipine via oxidation of the pyridine ring. Ragno at 20. The chemical structure of Amlodipine Related Substance A (viz., Impurity A) is shown below.

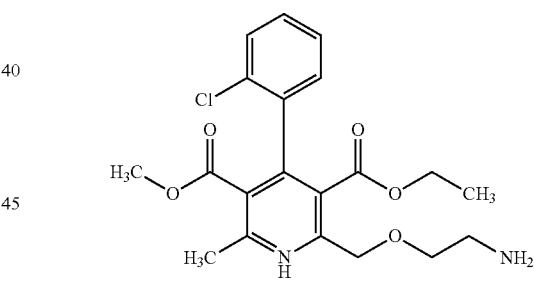

The Impurity A related substance does not show any significant calcium antagonist activity relative to amlodipine. Stopher at S59. Additional amlodipine degradation impurities have been reported in the literature. See, e.g., Rapolu at 61 (reporting rearrangement products) and Murakami at 75 (reporting Maillard reaction product between amlodipine and a reducing disaccharide).

Amlodipine itself is not satisfactory in photostability and preservation stability, and various salts are formed to improve them. For example, Davison teaches that besylate salt and maleate salt are preferable from among various salts of amlodipine, including tosylate, succinate, salicylate, maleate, acetate, and hydrochloride.

Nahata reports the stability of amlodipine besylate in two suspension dosage forms. Particularly, Nahata reported stabilities of extemporaneous dosage forms prepared from crushed NORVASC® tablets in two different vehicles. Based on the results presented therein, Nahata found that the prepared amlodipine suspension dosage forms were stable for 91 days under refrigerated conditions (4° C.) or 56 days at room temperature (25° C.).

Another salt form, amlodipine benzoate, is also commercially available in the United States under the brand name KATERZIA® (amlodipine) oral suspension. KATERZIA® contains 1.30 mg/mL amlodipine benzoate, equivalent to 1 mg/mL amlodipine, as well as the following inactive ingredients: citric acid, colloidal silicon dioxide, hypromellose, maltodextrin, polysorbate 80, simethicone, sodium benzoate, sodium besylate, sodium citrate, sodium hydroxide, sucralose, and water as inactive ingredients. See KATERZIA® Label; see also Brauer. KATERZIA® is a white to off-white oral suspension. The KATERZIA® Prescribing Information states that KATERZIA® "should be stored refrigerated (2° C. to 8° C./36° F. to 46° F.). Avoid freezing and excessive heat. Protect from light." Because KATERZIA® is a suspension product, the KATERZIA® Label states that the end user should shake before using.

Tatsumi describes an aqueous oral preparation (jelly preparation) of amlodipine, which is reportedly stable and rapidly disintegrable. The amlodipine stability may be improved by using an anionic surfactant having a sulfuric acid group or a sulfonic acid group (e.g., sodium lauryl sulfate) as a stabilizer in an aqueous solution of amlodipine, preparing a liquid stable in the range of pH 5-7 as the liquid property, and adding and mixing a gelling agent, a fine powder solid and a gelling regulator.

Davison reports a sterile aqueous solution containing amlodipine besylate for parenteral administration that includes 10 to 40% by volume of propylene glycol and about 1% w/v of sodium chloride.

Noburu describes a solution of amlodipine besylate having propylene glycol and a sugar alcohol as essential components, as well as water in an amount that ranges from 10% to 60% by weight. Stability tests (at 60° C. for 14-days) of compositions disclosed therein showed that amlodipine besylate is incompatible with glycerin showing discoloration, precipitation, and an increased impurity level.

Mandal describes amlodipine liquid formulations containing glycerin, maltitol, butylated hydroxy toluene, a flavoring agent, water, and optionally ethanol. The amount of water in the Mandal amlodipine liquid formulations is about 11% w/w. Results show that the Mandal formulations provide for unacceptable impurity levels. Results presented herein provide a basis for better understanding the unacceptable impurity levels of Mandal's amlodipine formulations.

Presently, there is no commercial product of amlodipine available in liquid oral solution form. As stated above, amlodipine is available in solid tablet dosage form (Norvasc®). The currently marketed amlodipine tablet may be difficult to swallow by the pediatric and geriatric populations, as well as by patients with swallowing impediments and blockages and is in critical condition.

Also as stated above, amlodipine is available in a suspension dosage form (KATERZIA®), but KATERZIA® requires strict storage conditions including refrigeration. One may appreciate that a suspension dosage form may be disadvantageous with respect to dose uniformity because of sedimentation and poor dispersibility. The lack of dose uniformity may result in an incorrect dosage amount, and thus, may be problematic for the treatment of a patient with hypertension and/or coronary artery disease at least because a satisfactory therapeutic effect may not be achieved.

Despite a market demand for alternative oral formulations, there is no commercially available amlodipine-containing oral solution dosage form. The oral solution dosage form addresses patients that have difficulty swallowing tablets. Further, an oral solution dosage form addresses potential problems associated with a suspension product because it provides assurance of dosage uniformity upon administration to patients and eliminates difficulty of administration.

While investigating amlodipine-containing oral solution dosage forms, it was discovered that amlodipine stability depends on the inactive ingredients present in the formulation. The liquid formulations disclosed herein serve to solve the above-mentioned drawbacks of prior amlodipine-containing formulations.

SUMMARY

Disclosed herein is a liquid pharmaceutical formulation substantially free of water, comprising: (i) amlodipine or a pharmaceutically acceptable salt thereof, (ii) at least one pharmaceutically acceptable excipient, and (iii) a sufficient amount of a vehicle comprising glycerin. Also disclosed herein is a liquid pharmaceutical formulation substantially free of water and ethanol, comprising: (i) amlodipine or a pharmaceutically acceptable salt thereof, (ii) at least one pharmaceutically acceptable excipient, and (iii) a sufficient amount of a vehicle comprising glycerin.

DEFINITIONS

As used herein, the singular forms "a," "an," and "the" include plural references unless the context clearly dictates otherwise. Unless defined otherwise, all technical and scientific terms used herein have the same meanings as commonly understood by one of ordinary skill in the art.

The expression "substantially free of water," as used herein, refers to an amount of water less than or equal to about 5% w/w of the total weight of the formulation, including about 4% w/w, about 3% w/w, about 2% w/w, about 1% w/w, about 0.5% w/w, about 0.1% w/w, and about 0.01% w/w or lower (e.g., about 0% w/w of water).

The expression "substantially free of ethanol," as used herein, refers to an amount of ethanol less than or equal to about 5% w/w of the total weight of the formulation, including about 4% w/w, about 3% w/w, about 2% w/w, about 1% w/w, about 0.5% w/w, about 0.1% w/w, and about 0.01% w/w or lower (e.g., about 0% w/w of ethanol).

The expression "% w/w," as used herein, refers to the percent of the weight of an identified component based on the total weight of the formulation.

The expressions "optional" or "optionally" means that the subsequently described event or circumstance may or may not occur, and that the description includes instances where the event occurs and instances where it does not.

The expression "pharmaceutically acceptable," as used herein refers to an excipient having compatibility with the other ingredients of the formulation and not deleterious to the recipient thereof.

DETAILED DESCRIPTION

Disclosed herein is a liquid pharmaceutical formulation substantially free of water, comprising: (i) amlodipine or a pharmaceutically acceptable salt thereof, (ii) at least one pharmaceutically acceptable excipient, and (iii) a sufficient amount of a vehicle comprising glycerin.

As related to amlodipine or a pharmaceutically acceptable salt thereof and the at least one pharmaceutically acceptable excipient, the liquid pharmaceutical formulation is in the form of a solution.

In one aspect, the amount of amlodipine or a pharmaceutically acceptable salt thereof, based on amlodipine, ranges from about 0.001% w/w to about 0.5% w/w based on the total weight of the formulation, and all values in between, for example, about 0.002% w/w, about 0.003% w/w, about 0.004% w/w, about 0.005% w/w, about 0.006% w/w, about 0.007% w/w, about 0.008% w/w, about 0.009% w/w, about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.10% w/w, about 0.11% w/w, about 0.12% w/w, about 0.13% w/w, about 0.14% w/w, about 0.15% w/w, about 0.16% w/w, about 0.17% w/w, about 0.18% w/w, about 0.19% w/w, about 0.20% w/w, about 0.21% w/w, about 0.22% w/w, about 0.23% w/w, about 0.24% w/w, about 0.25% w/w, about 0.26% w/w, about 0.27% w/w, about 0.28% w/w, about 0.29% w/w, about 0.30% w/w, about 0.31% w/w, about 0.32% w/w, about 0.33% w/w, about 0.34% w/w, about 0.35% w/w, about 0.36% w/w, about 0.37% w/w, about 0.38% w/w, about 0.39% w/w, about 0.40% w/w, about 0.41% w/w, about 0.42% w/w, about 0.43% w/w, about 0.44% w/w, about 0.45% w/w, about 0.46% w/w, about 0.47% w/w, about 0.48% w/w, and about 0.49% w/w.

In another aspect, the amount of amlodipine or a pharmaceutically acceptable salt thereof, based on amlodipine, ranges from about 0.005% w/w to about 0.15% w/w.

In yet another aspect, the amount of amlodipine or a pharmaceutically acceptable salt thereof, based on amlodipine, ranges from about 0.08% w/w to about 0.12% w/w.

Pharmaceutically acceptable salts of amlodipine include, but are not limited to, amlodipine besylate, amlodipine maleate, amlodipine benzoate, amlodipine tosylate, amlodipine succinate, amlodipine salicylate, amlodipine acetate, and amlodipine hydrochloride, as well as other pharmaceutically acceptable salts described, for example, by Berge.

In one aspect, a pharmaceutically acceptable salt relates to amlodipine besylate. For ease of reference, the reported molecular weight of amlodipine besylate is 567.1 g/mol ("ABMW"), while the reported molecular weight of amlodipine is 408.879 g/mol ("AMW"). One may readily convert an amount of amlodipine besylate to an amount of amlodipine by multiplying the amount of amlodipine besylate by a factor that corresponds to the ratio of the respective molecular weights of amlodipine and amlodipine besylate (viz., AMW/ABMW=408.879/567.1≈0.72).

Liquid formulations disclosed herein result in an amlodipine stability heretofore not observed. For instance, a formulation disclosed herein has an amlodipine content of: (i) 100±10% amlodipine labeled content when stored for about 24-months at 25±2° C. and 60±5% relative humidity; (ii) 100±10% amlodipine labeled content when stored for about 18-months at 25±2° C. and 60±5% relative humidity; (iii) 100±10% amlodipine labeled content when stored for about 12-months at 25±2° C. and 60±5% relative humidity; (iv) 100±5% amlodipine labeled content when stored for about 24-months at 25±2° C. and 60±5% relative humidity; (v) 100±5% amlodipine labeled content when stored for about 18-months at 25±2° C. and 60±5% relative humidity; (vi) 100±5% amlodipine labeled content when stored for about 12-months at 25±2° C. and 60±5% relative humidity; (vi) 100±5% amlodipine labeled content when stored for about 12-months at 30±2° C. and 65±5% relative humidity; and/or (vii) 100±5% amlodipine labeled content when stored for about 6-months at 40±2° C. and 75±5% relative humidity.

One may appreciate that the amlodipine labeled content refers to the stated amount of amlodipine present in the formulation. Thus, a liquid formulation that contains about 0.1% w/w amlodipine by weight of the formulation relates to the labeled content. Thus, 100±10% of labeled content of about 0.1% w/w corresponds to an amount of amlodipine of about 0.09% w/w to about 0.11% w/w (or 0.1±0.01% w/w).

In certain embodiments, it may be convenient to identify the amlodipine labeled content in terms of a mass amount per unit volume, such as, for example, 5 mg amlodipine per 5 mL of formulation or 1 mg amlodipine per 1 mL of formulation. One may convert the amount of amlodipine expressed as a percent based on the total weight of the formulation (e.g., amlodipine % w/w) by multiplying the amlodipine amount (in % w/w) by 10-times the stated solution density. As an example, if the formulation contains about 0.08% w/w amlodipine and the solution density is about 1.25 g/mL, then the amount of amlodipine in the solution is about 1 mg/mL. Thus, 100±10% of labeled content of about 1 mg amlodipine per 1 mL of formulation corresponds to an amount of amlodipine of about 0.9 mg/mL to about 1.1 mg/mL (or 1.0±0.1 mg/mL).

Liquid formulations disclosed herein result in a reduced amount of Amlodipine Related Substance A (viz., Impurity A). For instance, a formulation disclosed herein has an amount of Impurity A of: (i) not more than about 3% w/w when stored for about 24-months at 25±2° C. and 60±5% relative humidity; (ii) not more than about 3% w/w when stored for about 18-months at 25±2° C. and 60±5% relative humidity; (iii) not more than about 3% w/w when stored for about 12-months at 25±2° C. and 60±5% relative humidity; (iv) not more than about 1% w/w when stored for about 24-months at 25±2° C. and 60±5% relative humidity; (v) not more than about 1% w/w when stored for about 18-months at 25±2° C. and 60±5% relative humidity; (vi) not more than about 1% w/w when stored for about 12-months at 25±2° C. and 60±5% relative humidity; (vi) not more than about 1% w/w when stored for about 12-months at 30±2° C. and 65±5% relative humidity; and/or (vii) not more than about 1% w/w when stored for about 6-months at 40±2° C. and 75±5% relative humidity.

The liquid formulations disclosed herein comprise at least one pharmaceutically acceptable excipient, which may include a sweetener agent, an antioxidant, a co-solvent, a flavoring agent, or a combination thereof.

The amount of a sweetener agent, if present, ranges from about 0% w/w to about 11% w/w, based on the total weight of the formulation, and all values in between, for example, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3.0% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5.0% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6.0% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7.0% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8.0% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9.0% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, about 10.0% w/w, about 10.1% w/w, about 10.2% w/w, about 10.3% w/w, about 10.4% w/w, about 10.5% w/w, about 10.6% w/w, about 10.7% w/w, about 10.8% w/w, and about 10.9% w/w.

Examples of sweetener agents include, but are not limited to acesulfame potassium, alitame, aspartame, compressible sugar, confectioner's sugar, dextrose, erythritol, fructose, glycerin, glycine, inulin, isomalt, lactitol, liquid glucose, maltitol, maltitol solution, a maltitol oligomer, maltose, mannitol, neohesperidin dihydrochalcone, neotame, saccharin, saccharin sodium, sodium cyclamate, sorbitol, sucralose, sucrose, tagatose, thaumatin, trehalose, and xylitol.

In one aspect, the sweetener agent comprises maltitol. The Handbook explains that maltitol may be commercially available as a solid (e.g., Amalty; Maltbit, Maltisorb, among others) and as a liquid solution (e.g., Finmalt L, Lycasin HBC, Lycasin 80/55, among others). The Handbook describes maltitol-containing compositions, including, for example Lycasin® 80/55 (alternatively referred to herein as liquid maltitol), which comprises a dried content of about 75% and a maltitol content of about 52% w/w, as well as a specific gravity of about 1.36 at 20° C. See the Handbook at 416-417; see also Serpelloni and Dodd. One may appreciate that liquid maltitol contains a certain amount of water, e.g., 25% w/w. One may appreciate that solid maltitol may be used in place of liquid maltitol.

In one aspect, the sweetener agent comprises maltitol in an amount of from about 5.5% w/w to about 7.0% w/w, and all values in between, for example, about 5.6% w/w, about 5.7% w/w, about 5.8% w/w, about 5.9% w/w, about 6.1% w/w, about 6.2% w/w, about 6.3% w/w, about 6.4% w/w, about 6.5% w/w, about 6.6% w/w, about 6.7% w/w, about 6.8% w/w, and about 6.9% w/w.

In another aspect, the sweetener agent comprises glycyrrhizic acid, which is commercially available under the tradename Magnasweet®. Magnasweet® 110 contains from 8.5 to 10% w/w monoammonium glycyrrhizinate, as measured by the content of glycyrrhizic acid, in a vehicle comprising glycerin having a specific gravity of about 1.27 at 20° C. A typical amount of monoammonium glycyrrhizinate, as measured by the content of glycyrrhizic acid, found in Magnasweet® 110 is about 9.9% w/w.

An antioxidant, if present, ranges from about 0.01% w/w to about 0.1% w/w and all values in between, for example, about 0.02% w/w, about 0.03% w/w, about 0.04% w/w, about 0.05% w/w, about 0.06% w/w, about 0.07% w/w, about 0.08% w/w, and about 0.09% w/w.

Examples of antioxidants include, but are not limited to, ascorbyl palmitate, butylated hydroxyanisole, butylated hydroxytoluene, erythorbic acid, ethyl oleate, methionine, monothioglycerol, propyl gallate, sodium ascorbate, thymol, tocopherol (e.g., alpha tocopherol), vitamin E, and vitamin E polyethylene glycol succinate.

In one aspect, the antioxidant comprises butylated hydroxyanisole in an amount of about 0.01% w/w to 0.1% w/w and all values in between. In another aspect, the antioxidant comprises butylated hydroxyanisole in an amount of about 0.03% w/w to about 0.04% w/w.

Examples of a co-solvent include, but are not limited to, an alcohol (e.g., ethanol), a glycol (e.g., propylene glycol, ethylene glycol, and a polyethylene glycol), and the like.

A co-solvent, if present, ranges from about 1 to about 15% w/w, based on the total weight of the formulation, and all values in between, for example, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3.0% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5.0% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6.0% w/w, about 6.1% w/w, about 6.2% w/w, about 6.3% w/w, about 6.4% w/w, about 6.5% w/w, about 6.6% w/w, about 6.7% w/w, 6.8% w/w, about 6.9% w/w, about 7.0% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8.0% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9.0% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, about 10.0% w/w, about 10.1% w/w, about 10.2% w/w, about 10.3% w/w, about 10.4% w/w, about 10.5% w/w, about 10.6% w/w, about 10.7% w/w, about 10.8% w/w, about and 10.9% w/w, about 11.0% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12.0% w/w, about 12.1% w/w, about 12.2% w/w, about 12.3% w/w, about 12.4% w/w, about 12.5% w/w, about 12.6% w/w, about 12.7% w/w, about 12.8% w/w, about 12.9% w/w, about 13.0% w/w, about 13.1% w/w, about 13.2% w/w, about 13.3% w/w, about 13.4% w/w, about 13.5% w/w, about 13.6% w/w, about 13.7% w/w, about 13.8% w/w, about 13.9% w/w, about 14.0% w/w, about 14.1% w/w, about 14.2% w/w, about 14.3% w/w, about 14.4% w/w, about 14.5% w/w, about 14.6% w/w, about 14.7% w/w, about 14.8% w/w, about and about 14.9% w/w.

Examples of flavoring agents include, but are not limited to, cherry, orange, banana, strawberry or other acceptable fruit flavors, or mixtures of cherry, orange, and other acceptable fruit flavors. Additional examples of flavoring agents include, but are not limited to, cinnamon oil, oil of wintergreen, peppermint oils, clove oil, bay oil, anise oil, *eucalyptus*, thyme oil, cedar leaf oil, oil of nutmeg, oil of sage, oil of bitter almonds, and *cassia* oil and the like or any combinations thereof. Further examples of flavoring agents include, but are not limited to, vanilla, citrus oil, including lemon, orange, grape, lime and grapefruit, and fruit essences, including apple, banana, pear, peach, strawberry, raspberry, cherry, plums pineapple, apricot, peppermint, Tutti Frutti flavor, mixed berry, and so forth and the like or any combinations thereof. Solid forms, such as spray dried forms of flavoring agents, may also be useful in the liquid dosage forms disclosed herein.

A flavoring agent, if present, ranges from about 0.001 to about 0.020% w/w, based on the total weight of the formulation, and all values in between, for example, about 0.002% w/w, about 0.003% w/w, about 0.004% w/w, about 0.005% w/w, about 0.006% w/w, about 0.007% w/w, about 0.008% w/w, about 0.009% w/w, about 0.01% w/w, about 0.011% w/w, about 0.012%, about 0.013% w/w, about 0.014% w/w, about 0.015% w/w, about 0.016% w/w, about 0.017% w/w, about 0.018% w/w, and about 0.019% w/w.

The vehicle comprising glycerin may be present in a sufficient (viz., Q.S.) amount to achieve a stated ingredient concentration, e.g., amlodipine concentration. A sufficient amount of a vehicle comprising glycerin includes for example, an amount of glycerin that ranges from about 73% w/w to about 99% w/w, and all values in between, for example, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w, about 91% w/w, about 92% w/w, about 93% w/w, about 94% w/w, about 95% w/w, about 96% w/w, about 97% w/w, and about 98% w/w.

In one aspect related to the vehicle comprising glycerin, the glycerin may be present in an amount selected from the group consisting of about 77% w/w, about 84% w/w, about 85% w/w, and about 86% w/w.

One aspect relates to a liquid pharmaceutical formulation substantially free of water, comprising: about 0.07 to about 0.2% w/w of amlodipine besylate; about 4% w/w to about 7% w/w of a sweetening agent; about 0.01% to about 0.05% w/w of an antioxidant; optionally about 0.006% w/w to about 0.010% w/w of a flavoring agent; optionally about 2% w/w to about 4% w/w ethanol; and a sufficient amount of a vehicle comprising glycerin.

Another aspect relates to a liquid pharmaceutical formulation substantially free of water, comprising: about 0.08 to about 0.14% w/w of amlodipine besylate; about 4% w/w to about 7% w/w of a sweetening agent; about 0.01% to about 0.05% w/w of an antioxidant; optionally about 0.006% w/w to about 0.010% w/w of a flavoring agent; optionally about 2% w/w to about 4% w/w ethanol; and a sufficient amount of a vehicle comprising glycerin.

Yet another aspect relates to a liquid pharmaceutical formulation substantially free of water, comprising: about 0.10 to about 0.12% w/w of amlodipine besylate; about 4% w/w to about 7% w/w of a sweetening agent; about 0.01% to about 0.05% w/w of an antioxidant; optionally about 0.006% w/w to about 0.010% w/w of a flavoring agent; optionally about 2% w/w to about 4% w/w ethanol; and a sufficient amount of a vehicle comprising glycerin.

Another aspect relates to a liquid pharmaceutical formulation substantially free of water, comprising: about 0.10 to about 0.12% w/w of amlodipine besylate; about 4% w/w to about 7% w/w of a sweetening agent; about 0.03% to about 0.04% w/w of an antioxidant; optionally about 0.006% w/w to about 0.010% w/w of a flavoring agent; optionally about 2% w/w to about 4% w/w ethanol; and a sufficient amount of a vehicle comprising glycerin.

And yet another aspect relates to a liquid pharmaceutical formulation substantially free of water, comprising: about 0.11% w/w of amlodipine besylate; about 4% w/w to about 7% w/w of a sweetening agent; about 0.01% to about 0.05% w/w of an antioxidant; optionally about 0.006% w/w to about 0.010% w/w of a flavoring agent; optionally about 2% w/w to about 4% w/w ethanol; and a sufficient amount of a vehicle comprising glycerin.

And yet another aspect relates to a liquid pharmaceutical formulation substantially free of water, comprising: about 0.11% w/w of amlodipine besylate; about 4% w/w to about 7% w/w of a sweetening agent comprising maltitol; about 0.01% to about 0.05% w/w of an antioxidant comprising butylated hydroxyanisole; optionally about 0.006% w/w to about 0.010% w/w of a flavoring agent; optionally about 2% w/w to about 4% w/w ethanol; and a sufficient amount of a vehicle comprising glycerin.

A further aspect relates to a liquid pharmaceutical formulation substantially free of water, comprising: about 0.11% w/w of amlodipine besylate; about 5% w/w to about 7% w/w of a sweetening agent comprising maltitol; about 0.03% w/w of an antioxidant comprising butylated hydroxyanisole; optionally about 0.008% w/w to about 0.010% w/w of a flavoring agent; optionally about 2% w/w to about 4% w/w ethanol; and a sufficient amount of a vehicle comprising glycerin.

An additional aspect relates to a liquid pharmaceutical formulation substantially free of water, comprising: about 0.08% w/w of amlodipine; as its besylate salt; about 5% w/w to about 7% w/w of a sweetening agent comprising maltitol; about 0.03% w/w of an antioxidant comprising butylated hydroxyanisole; optionally about 0.008% w/w to about 0.010% w/w of a flavoring agent; about 2.5% w/w ethanol; and a sufficient amount of a vehicle comprising glycerin.

An additional aspect relates to a liquid pharmaceutical formulation substantially free of water, comprising: about 0.08% w/w of amlodipine; as its besylate salt; about 6% w/w of a sweetening agent comprising maltitol; about 0.03% w/w of an antioxidant comprising butylated hydroxyanisole; about 0.008% w/w to about 0.010% w/w of a flavoring agent; about 2.5% w/w ethanol; and a sufficient amount of a vehicle comprising glycerin.

An additional aspect relates to a liquid pharmaceutical formulation substantially free of water, comprising: about 0.08% w/w of amlodipine; as its besylate salt; about 11% w/w of a liquid maltitol syrup comprising maltitol; about 0.03% w/w of an antioxidant comprising butylated hydroxyanisole; about 0.008% w/w to about 0.010% w/w of a flavoring agent; about 2.5% w/w ethanol; and a vehicle comprising about 86% w/w amount of glycerin.

In an alternative embodiment, it may be desirable to reduce the amount of water and ethanol in a formulation.

Accordingly, disclosed herein is a liquid pharmaceutical formulation substantially free of water and ethanol, comprising: (i) amlodipine or a pharmaceutically acceptable salt thereof, (ii) at least one pharmaceutically acceptable excipient, and (iii) a sufficient amount of a vehicle comprising glycerin.

One aspect relates to a liquid pharmaceutical formulation substantially free of water and ethanol, comprising: about 0.05% w/w to about 0.15% w/w of amlodipine besylate; about 0.01% to about 0.07% w/w of an antioxidant; about 0.005% w/w to about 0.015% w/w of a flavoring agent; about 4% w/w to about 10% w/w of a glycol; and a sufficient amount of a vehicle comprising glycerin.

Yet another aspect relates to a liquid pharmaceutical formulation substantially free of water and ethanol, comprising: about 0.07% w/w to about 0.13% w/w of amlodipine besylate; about 0.02% w/w to about 0.06% w/w of an antioxidant; about 0.007% w/w to about 0.013% w/w of a flavoring agent; about 5% w/w to about 9% w/w of a glycol; and a sufficient amount of a vehicle comprising glycerin.

And yet another aspect relates to a liquid pharmaceutical formulation substantially free of water and ethanol, comprising: about 0.08% w/w to about 0.12% w/w of amlodipine besylate; about 0.03% w/w to about 0.05% w/w of an antioxidant; about 0.009% w/w to about 0.011% w/w of a flavoring agent; about 6% w/w to about 8% w/w of a glycol comprising propylene glycol; and a sufficient amount of a vehicle comprising glycerin.

Another aspect relates to a liquid pharmaceutical formulation substantially free of water and ethanol, comprising: about 0.09% w/w to about 0.11% w/w of amlodipine besylate; about 0.04% w/w of an antioxidant comprising butylated hydroxyanisole; about 0.01% w/w of a flavoring agent; about 7% w/w of a glycol comprising propylene glycol; and a sufficient amount of a vehicle comprising glycerin.

And yet another aspect relates to a liquid pharmaceutical formulation substantially free of water and ethanol, comprising: about 0.10% w/w of amlodipine besylate; about 0.04% w/w of an antioxidant comprising butylated hydroxyanisole; about 0.01% w/w of a flavoring agent; about 7% w/w of propylene glycol; and a vehicle comprising about 91% w/w to about 93% w/w of a glycerin.

The liquid formulation substantially free of water and ethanol results in an amlodipine stability heretofore not observed. For instance, the liquid formulation substantially free of water and ethanol has an amlodipine content of: (i) 100±10% labeled content when stored for about 24-months at 25±2° C. and 60±5% relative humidity; (ii) 100±10% labeled content when stored for about 18-months at 25±2° C. and 60±5% relative humidity; (iii) 100±10% labeled content when stored for about 12-months at 25±2° C. and 60±5% relative humidity; (iv) 100±5% labeled content when stored for about 24-months at 25±2° C. and 60±5% relative humidity; (v) 100±5% labeled content when stored for about 18-months at 25±2° C. and 60±5% relative humidity; (vi) 100±5% labeled content when stored for about 12-months at 25±2° C. and 60±5% relative humidity; (vi) 100±5% labeled content when stored for about 12-months at 30±2° C. and 65±5% relative humidity; and/or (vii) 100±5% labeled content when stored for about 6-months at 40±2° C. and 75±5% relative humidity.

The liquid formulation substantially free of water and ethanol results in an amlodipine stability heretofore not observed. For instance, the liquid formulation substantially free of water and ethanol has an amount of Impurity A of: (i) not more than about 3% w/w when stored for about 24-months at 25±2° C. and 60±5% relative humidity; (ii) not more than about 3% w/w when stored for about 18-months at 25±2° C. and 60±5% relative humidity; (iii) not more than about 3% w/w when stored for about 12-months at 25±2° C. and 60±5% relative humidity; (iv) not more than about 1% w/w when stored for about 24-months at 25±2° C. and 60±5% relative humidity; (v) not more than about 1% w/w when stored for about 18-months at 25±2° C. and 60±5% relative humidity; (vi) not more than about 1% w/w when stored for about 12-months at 25±2° C. and 60±5% relative humidity; (vi) not more than about 1% w/w when stored for about 12-months at 30±2° C. and 65±5% relative humidity; and/or (vii) not more than about 1% w/w when stored for about 6-months at 40±2° C. and 75±5% relative humidity.

The formulations described herein may be stored in a pharmaceutically acceptable closure system, such as, for example, an amber PET bottle or an amber glass bottle. The bottle volume is, for example, about 150 mL to about 200 mL, e.g., 185 mL, with a formulation volume of about 150 mL. An amber colored bottle has a light transmission of, for example, less than 5%, less than 4%, less than 3%, less than 2%, or less than 1% at any wavelength between 290 nm and 450 nm.

One aspect relates to a bottled product comprising a formulation described herein. In one aspect, the bottled product comprises an amber glass bottle (see DMF No. 14003) with a pharmaceutically acceptable closure (such as a 28 mm Polypropylene TE-CRC cap with EPE liner, see DMF No. 18371).

Another aspect relates to a container comprising written material and a bottle comprising any one of the formulations disclosed herein. The written material includes, among other things, a description of the formulation and indications for use of the formulation, as summarized below.

Indications

The formulations disclosed herein may be used for the treatment of hypertension in adults and children 6 years and older. See the NORVASC® and KATERZIA® Labels. Additionally, the formulations disclosed herein also may be used in combination with other antihypertensive agents.

Examples of other antihypertensive agents include, but are not limited to a loop diuretic, e.g., bumetanide, ethacrynic acid, furosemide, torsemide; a thiazide diuretic, e.g., epitizide, hydrochlorothiazide, chlorothiazide, bendroflumethiazide, methyclothiazide, polythiazide; a thiazide-like diuretics, e.g., indapamide, chlorthalidone, metalozone, xipamide, clopamide, a potassium-sparing diuretic, e.g., amiloride, triamterene, spironolactone, eplerenone; an ACE inhibitor, e.g., captopril, enalapril, fosinopril, lisinopril, moexipril, perindopril, quinapril, ramipril, trandolapril, benazepril; an angiotensin II receptor antagonist, e.g., azilsartan, candesartan, eprosartan, irbesartan, losartan, olmesartan, telmisartan, valsartan, fimasartan; an adrenergic receptor antagonists, e.g., a beta blockers, e.g., acebutolol, atenolol, bisoprolol, betaxolol, carteolol, carvedilol, labetalol, metoprolol, nadolol, nebivolol, oxprenolol, penbutolol, pindolol, propranolol, timolol; an alpha blocker, e.g., doxazosin, phentolamine, indoramin, phenoxybenzamine, prazosin, terazosin, tolazoline, a mixed alpha+beta blockers, e.g., bucindolol, carvedilol, labetalol, among others.

The formulations disclosed herein further may be used for either the symptomatic treatment of chronic stable angina the treatment of confirmed or suspected vasospastic angina consistent with the NORVASC® and KATERZIA® Labels. Additionally, the formulations disclosed herein also may be used in combination with other antianginal agents.

Examples of antianginal agents include, but are not limited to nitrates e.g., isosorbide dinitrate, isosorbide mononitrate, and nitroglycerin; a calcium antagonist e.g., diltiazem, nifedipine, nimodipine, and verapamil; a beta blockers, e.g., atenolol, pindolol, propranolol, and metoprolol; ranolazine; among others.

The formulations disclosed herein further may be used for the treatment of confirmed or suspected vasospastic angina.

In view of the foregoing, an aspect disclosed herein relates to a method for the treatment of hypertension in a patient in need thereof, which comprises administering to said patient a therapeutically effective amount of any one of the formulations disclosed herein. With respect to this indication, and other indications contemplated herein, the patient may be an adult patient (including a geriatric patient) and the patient may be a pediatric patient.

Generally, the expression "therapeutically effective amount" refers to an amount of amlodipine sufficient to treat any one of the conditions disclosed herein.

As related to the treatment of hypertension, a therapeutically effective amount refers to the patient population in question. For instance, the usual initial antihypertensive oral dose of amlodipine is 5 mg orally once daily, and the maximum dose is 10 mg once daily. Alternatively, for small, fragile, or elderly patients, or patients with hepatic insufficiency the amlodipine dose may be started on 2.5 mg once daily and this dose may be used when adding the amlodipine formulation disclosed herein in combination with another antihypertensive therapy.

Another aspect disclosed herein relates to a method for the treatment of hypertension in a patient in need thereof, which comprises administering to said patient a therapeutically effective amount of any one of the formulations disclosed herein in combination with an antihypertensive agent. An effective antihypertensive oral dose in a pediatric patient (ages 6 to 17 years) is 2.5 to 5 mg once daily.

Another aspect disclosed herein relates to a method for the symptomatic treatment of a chronic stable angina in a patient in need thereof, which comprises administering to said patient a therapeutically effective amount of any one of the formulations disclosed herein.

Yet another aspect disclosed herein relates to a method for the treatment of confirmed or suspected vasospastic angina in a patient in need thereof, which comprises administering to said patient a therapeutically effective amount of any one of the formulations disclosed herein.

For either one of these two conditions (viz., symptomatic treatment of a chronic stable angina and of confirmed or suspected vasospastic angina), a therapeutically effective corresponds to an amlodipine dose of 5 to 10 mg once daily, with the lower dose suggested in the elderly and in patients with hepatic insufficiency. Most patients will require 10 mg once daily for adequate effect.

In some instances, the formulations disclosed herein may be useful for the treatment of a coronary artery disease (CAD). Accordingly, another aspect relates to a method for the treatment a coronary artery disease in a patient in need thereof, which comprises administering to said patient a therapeutically effective amount of any one of the formulations disclosed herein. In a patient with recently documented CAD by angiography and without heart failure or an ejection fraction <40%, administration of an amlodipine-containing formulation disclosed herein is indicated to reduce the risk of hospitalization for angina and to reduce the risk of a coronary revascularization procedure. The recommended dose range for patients with coronary artery disease is 5 to 10 mg once daily.

In some instances, the formulations disclosed herein may be useful for the treatment of angina and/or high blood pressure when administered in combination with a therapeutically effective amount of a statin. Examples of statins include, but are not limited to atorvastatin, fluvastatin, lovastatin, pitavastatin, pravastatin, rosuvastatin, and simvastatin.

Processes for Preparation

In another embodiment, the formulation disclosed herein may be prepared by the process comprising the steps of:
a) adding a suitable amount of a vehicle comprising glycerin in a first vessel;
b) adding a suitable amount of a co-solvent in a second vessel;
c) adding a suitable amount of antioxidant to the second vessel of step b);
d) adding a suitable amount of amlodipine besylate to the second vessel of step c);
e) adding a suitable amount of a vehicle comprising glycerin to the second vessel of step d);
f) transferring the contents of the second vessel of step d) to the first vessel of step a);
g) optionally adding a sweetener to the first vessel of step f);
h) optionally adding a flavoring agent to the first vessel of step g); and
g) adding a remaining quantity of a vehicle comprising glycerin to make up the volume.

Additional processes for preparing the formulations disclosed herein are described in greater detail below.

Bioequivalence

One aspect relates to a liquid pharmaceutical formulation substantially free of water or substantially free of water and ethanol, comprising: (i) amlodipine or a pharmaceutically acceptable salt thereof, (ii) at least one pharmaceutically acceptable excipient, and (iii) a sufficient amount of a vehicle comprising glycerin; wherein administration of a dose to a subject comprising 10 mg of amlodipine exhibits at least one of the following characteristics: (a) a 90% Confidence Interval for the ratio of the mean AUC (0-72 h) which is between 80% and 125%; (b) a 90% Confidence Interval for the ratio of the mean Cmax, which is between 80% and 125%; wherein the ratio of the mean refers to an observable (viz., AUC (0-72 h) and/or Cmax) of the liquid formulation vs. the reference listed drug (e.g., NORVASC® (amlodipine besylate, 10 mg, tablet) for oral administration).

In one aspect, the liquid formulation comprises about 0.08% w/w of amlodipine; as its besylate salt; about 11% w/w of a liquid maltitol syrup comprising maltitol; about 0.03% w/w of an antioxidant comprising butylated hydroxyanisole; about 0.008% w/w to about 0.010% w/w of a flavoring agent; about 2.5% w/w ethanol; and a vehicle comprising about 86% w/w amount of glycerin; wherein upon administration of about 10 mL of formulation to a subject and separately the NORVASC® reference listed drug to the subject results in a 90% confidence interval of an ln-transformed geometric least squares mean for each of AUC (0-72 h) and Cmax that ranges from about 80% to about 125%.

In one aspect, the liquid formulation comprises about 0.08% w/w of amlodipine; as its besylate salt; about 11% w/w of a liquid maltitol syrup comprising maltitol; about 0.03% w/w of an antioxidant comprising butylated hydroxyanisole; about 0.008% w/w to about 0.010% w/w of a flavoring agent; about 2.5% w/w ethanol; and about 86% w/w amount of a vehicle comprising glycerin; wherein the liquid formulation is bioequivalent to the NORVASC® reference listed drug.

Formulation Development Work

As stated above, Mandal describes amlodipine liquid formulations containing glycerin, maltitol, butylated hydroxy toluene, a flavoring agent, water, and optionally ethanol. Also as stated above, results show that the Mandal formulations provide for unacceptable impurity levels. Results presented herein provide a basis for better understanding the unacceptable impurity levels of Mandal's amlodipine formulations.

Amounts of amlodipine and other components identified here were determined chromatographically, e.g., HPLC or GC.

The Assay of Amlodipine was determined using a high performance liquid chromatographic system (HPLC) equipped with a Waters Spherisorb ODS-2 (250×4.6) mm, 5 μm column and a Ultraviolet (UV, 237 nm) or diode array (PDA) detector, with a flow rate of 1.5 mL/min, an injection volume of 10 μL, a column oven temperature of 35° C., and an autosampler temperature of 25° C., a run time of 15 minutes, using a mobile phase comprised of Solution A and Solution B in the ratio of 30:70% v/v, respectively. Solution A comprised of an acetate buffer, while Solution B comprises acetonitrile. The acetate buffer was obtained by: (i) accurately weighing and transferring about 2.3 g of ammonium acetate into 1000 mL of water and mix; (ii) adding 1 mL of triethylamine into the solution of step (i) and mixing well; (iii) adjusting the pH of solution of step (ii) to 6.0±0.05 with diluted acetic acid; and (iv) filtering the solution of step (iii) through a 0.45 μm nylon membrane filter.

An amlodipine besylate standard (reference and working "AS") was prepared by: (i) accurately weighing and transferring about 70.0 mg of amlodipine besylate (reference/working) standard into a 100-mL volumetric flask, (ii) adding about 60 ml of diluent and sonicate to dissolve (diluent comprised of methanol and water in a ratio of 70:30% v/v, respectively); (iii) filling 100-mL volumetric flask to the mark with diluent and mixing well; (iv) pipetting out 5.0 mL of solution of step (iii) into a 25-mL volumetric flask, and (v) filling 25-mL volumetric flask to the mark with diluent and mixing well.

An amlodipine besylate sample ("AT") was prepared by: (i) accurately transferring 5.0 mL sample solution (e.g., a formulation described herein) into a 50.0 mL-volumetric flask; (ii) adding about 30.0 mL of diluent and sonicating for 5 minutes with intermittent shaking; (iii) filling the 50.0-mL volumetric flask to the mark with diluent and mixing well; and (iv) filtering the solution of step (iii) through 0.45 μm PVDF filter by discarding first 5 mL of filtrate.

Samples analyzed by HPLC, as described above, were used to calculate the % assay of amlodipine using the following formula.

% Assay of Amlodipine =

$$\left(\frac{AT}{AS}\right) \times \left(\frac{WS}{DS}\right) \times \left(\frac{DT}{WT}\right) \times \left(\frac{\left(\frac{Wt}{mL}\right)}{LC}\right) \times \left(\frac{409.0}{567.1}\right) \times P$$

where
AT: Mean peak area of Amlodipine obtained from sample preparation
AS: Mean peak area of Amlodipine obtained from standard preparation
WS: Weight of Amlodipine besylate reference/working standard taken in mg
DS: Dilution in standard preparation
DT: Dilution in sample preparation
WT: Weight of sample taken in mg
Wt/ml: Weight per milliliter of sample in mg/ml
LC: Label claim in mg/ml
409.0: Molecular weight of Amlodipine
567.1: Molecular weight of Amlodipine besylate
P: Potency of Amlodipine besylate reference/working standard Assay amounts of butylhydroxy anisole, as well as ethanol, were determined in a similar manner as explained above, with perhaps changes in mobile phases, diluents, and instrumentation (e.g., gas chromatography for ethanol). Likewise, percent amounts of impurities (e.g., Impurity A), were determined in a similar manner as explained above, except that the % impurity was calculated from the following expression:

$$\% \text{ Impurity} = \left(\frac{AT}{AS}\right) \times \left(\frac{WS}{DS}\right) \times \left(\frac{DT}{WT}\right) \times \left(\frac{\left(\frac{Wt}{mL}\right)}{LC}\right) \times \left(\frac{409.0}{567.1}\right) \times \left(\frac{1}{RRF}\right) \times P$$

where the variables are identified above, and RRF refers to the relative response factor. As a point of reference, the RRF-values for Amlodipine and Impurity A were 1.00 and 0.32, respectively. Additional parameters observed include retention time (min) of 47 (AML) and 31 (Imp. A).

Effect of Antioxidant on Liquid Solution of Amlodipine

Experiments were carried out to evaluate the effect of antioxidant on the stability of the liquid solution of amlodipine. Two batches were prepared: (i) Formulation A is with BHA as antioxidant and (ii) Formulation B is with BHT as antioxidant as mentioned in Table 1.

TABLE 1

Compositional makeup of Formulations A and B

| | Formulation ID: | |
|---|---|---|
| Ingredients | Form. A (4 L) Quantity (mg)/mL | Form. B (4 L) Quantity (mg)/mL |
| Amlodipine Besylate | 1.385† | 1.385† |
| Glycerin | 1000.0 | 1000.0 |
| Liquid Maltitol | 140.0 | 140.0 |
| BHT | 0.40 | — |
| BHA | — | 0.40 |
| Ethanol absolute* | 31.6‡ | 31.6‡ |
| Purified water | Qs to 1 mL | Qs to 1 mL |

Abbreviations: BHT (butylated hydroxytoluene) and BHA (butylated hydroxyanisole)
†Equivalent to 1.00 mg/mL amlodipine.
‡Corresponds to about 0.04 ml based on ethanol density of 0.790 g/mL.
Formulation density: 1.25 g/mL.

An exemplary process for preparing batches of Formulation A and Formulation B containing the above-mentioned ingredients is as follows.

1. Tare weight of SS manufacturing vessel S1: Add 98% of total batch size 3.92 Kg of glycerin to SS manufacturing vessel S1.

2. Tare weight of SS manufacturing vessel S2: Add about 127 g of ethanol absolute from total batch size in SS manufacturing vessel S2.

3. Add dispensed quantity of either BHT (about 1.6 g) or BHA (about 1.6 g) in manufacturing vessel S2 step 2, stir well until clear solution is obtained.

4. Add dispensed quantity of amlodipine besylate (about 5.540 g) in manufacturing vessel S2 step 3, stir well until hazy dispersion is obtained.

5. Add 80.0 gm of glycerin in manufacturing vessel S2, stir well until clear solution is obtained.

6. Transfer the content of SS manufacturing vessel S2 of step 5, to vessel S1 of step 1. Stir well until clear homogeneous solution is obtained.

7. Add dispensed quantity of Lycasin 80/55 (about 560 g corresponding to about 448 g of maltitol and about 112 g water) in manufacturing vessel S1 step 6, stir well until clear solution is obtained.

8. Add remaining quantity of purified water (about 227 g) to make up the volume 4 L (about 5040 g) and stirred by overhead stirrer in SS manufacturing vessel S1.

9. Filter the solution using 40-μm PP filter and filled in 150 mL Amber glass bottle with 28 mm CR cap.

N.B. The formulations identified above contain about 9% w/w of water.

Stability Study

The stability of Formulation A and Formulation B was evaluated by storing samples at 40±2° C. and 75%±5% RH for 3 months. Table 2 below summarizes the observed Assay values for each of amlodipine besylate ("AB"), butylated hydroxy toluene ("BHT Assay"), and butylated hydroxy anisole ("BHA Assay") with respect to labeled content, as well as the observed values for Impurity A, Single maximum unknown impurity ("SMUI"), and Total Impurities ("Tot. Imps.").

TABLE 2

Stability Results of Formulations A and B

| Parameters | Specification | Form. A | | Form. B | |
| --- | --- | --- | --- | --- | --- |
| | | Initial | 3M | Initial | 3M |
| Description | A clear pale straw colored, viscous liquid. | Unclear off white, viscous liquid. | Unclear off white, viscous liquid | A clear pale straw colored, viscous liquid | A clear pale straw colored, viscous liquid |
| AB Assay | NLT 90% and NMT 110% of 1.385 mg/mL | 98.3% | 94.9% | 98.4% | 95.3% |
| BHT Assay | NLT 80% and NMT 110% of 0.4 mg/mL | 83.4% | 22.5% | — | — |
| BHA Assay | NLT 80% and NMT 110% of 0.4 mg/mL | — | — | 99.4% | 91.9% |
| Ethanol content | NLT 90% and NMT 110% of 31.6 mg/mL | 94.8% | 90.1% | 96.1% | 92.2% |
| Organic impurities (By HPLC) | | | | | |
| Impurity-A | NMT 3.0% | 0.06% | 1.60% | 0.07% | 1.50% |
| SMUI | NMT 0.2% | 0.02% | 0.23% | ND | 0.11% |
| Tot. Imps. | NMT 3.5% | 0.16% | 2.19% | 0.07% | 1.87% |

After 3-month stability study under the stated conditions, it was observed that the composition containing BHT 0.4 mg/ml (Form. A) showed a higher level of single maximum unknown impurity as compared to the composition containing BHA 0.4 mg/mL (Form. B). Additionally, the BHT content decreased significantly (viz., 83.4% of labelled content vs. 22.5% of labelled content) after a three-month period. It was observed that when solution contains BHT, the total impurities, including maximum unknown impurity increased even at 3 months storage while the composition containing BHA showed a reduced amount of total impurities. The data suggests a difference in the formulation stability when antioxidant is changed from BHT to BHA. It should be noted that both Formulation A and Formulation B had an added water content of about 9% w/w.

As stated above, Mandal describes amlodipine liquid formulations containing glycerin, maltitol, butylated hydroxy toluene (BHT), a flavoring agent, water, and optionally ethanol. The amount of water in the Mandal amlodipine liquid formulations is about 11% w/w. Based on the data presented herein, it may be reasonable to conclude that the unacceptable impurity levels observed for Mandal's formulations may be due to the observed incompatibility of BHT and/or amlodipine in the presence of water. As water may be a culprit associated with reduced stability, an additional investigation considered evaluating the stability of amlodipine liquid formulations in the presence of water.

Effect of Water on Stability of Liquid Solution of Amlodipine

Experiments were carried out to evaluate the effect of purified water on the stability of the liquid solution of amlodipine. Two batches (Formulation C and Formulation D) were prepared—one with added water (Form. C) and the other without added water (Form. D), as shown in Table 3.

TABLE 3

Compositional makeup of Formulations C and D

| | Formulation ID: | |
| --- | --- | --- |
| | Form. C (4 L) | Form. D (4 L) |
| Ingredients | Quantity (mg)/mL | Quantity (mg)/mL |
| Amlodipine Besylate | 1.385† | 1.385† |
| Glycerin | 1000.0 | 1000.0 |
| Liquid Maltitol | 140.0 | 140.0 |
| BHA | 0.40 | 0.40 |
| Ethanol absolute | 31.6‡ | 31.6‡ |
| Purified water | Qs to 1 mL | — |
| Water Content (% w/w) | ≈9 | ≈3 |

Abbreviation: BHA (butylated hydroxyanisole).
†Equivalent to about 1 mg/mL amlodipine.
‡Corresponds to about 0.04 mL based on ethanol density of 0.790 g/mL.
Formulation density: 1.25 g/mL.

An exemplary process for preparing batches of Formulation C and Formulation D containing the above-mentioned ingredients is as follows.

1. Tare weight of SS manufacturing vessel S1: Add 98% of total batch size 3.92 kg of glycerin SS manufacturing vessel S1.

2. Tare weight of SS manufacturing vessel S2: Add 127 gm of ethanol absolute from total batch size in SS manufacturing vessel S2.

3. Add dispensed quantity of about 1.60 g of butylated hydroxyanisole in manufacturing vessel S2 step 2, stir well until clear solution is obtained.

4. Add dispensed quantity of about 5.54 g of amlodipine besylate in manufacturing vessel S2 step 3, stir well until hazy dispersion is obtained.

5. Add about 80.0 gm of glycerin in manufacturing vessel S2, stir well until clear solution is obtained.

6. Transfer the content of SS manufacturing vessel S2 of step 5, to vessel S1 of step 1. Stir well until clear homogeneous solution is obtained.

7. Add dispensed quantity of about 560 g of Lycasin 80/55 in manufacturing vessel S1 step 6, stir well until clear solution is obtained.

8a. For Formulation C, add remaining quantity of purified water to make up the volume 4 L=5 kg and stirred by overhead stirrer in SS manufacturing vessel S1.

8b. For Formulation D, add remaining quantity of glycerin to make up the volume 4 L=5 kg and stirred by overhead stirrer in SS manufacturing vessel S1.

9. Filter the solution using 40μ PP filter and filled in 150 mL Amber glass bottle with 28 mm CR cap.

Stability Study

The stability of Formulation C and Formulation D were evaluated by storing samples at 40±2° C. and 75%±5% RH for 3 months. The table below summarizes the observed Assay values for amlodipine besylate ("AB Assay") and butylated hydroxy anisole ("BHA Assay") with respect to labeled content, as well as the observed values for Impurity A, Single maximum unknown impurity ("SMUI"), and Total Impurities ("Tot. Imps.").

TABLE 4

Stability Results of Formulations C and D

|  |  | Form. C | | Form. D | |
| --- | --- | --- | --- | --- | --- |
| Parameters | Specification | Initial | 3M | Initial | 3M |
| AB Assay | NLT 90% and NMT 110% of 1.385 mg/mL | 98.4% | 95.3% | 97.3% | 97.3% |
| Impurity-A | NMT 3.0% | 0.07% | 1.50% | 0.05% | 0.58% |
| SMUI | NMT 0.2% | ND | 0.11% | 0.01% | 0.07% |
| Tot. Imps. | NMT 3.5% | 0.07% | 1.87% | 0.07% | 0.77% |

The data plainly shows that Formulation C (containing added water) showed increased degradation, with respect to an increased amount of Impurity A, as compared to the formulation without purified water (Formulation D). As stated above, the water content in Formulation C is about 9% w/w, while the water content in Formulation D is about 2% w/w. These data show that the presence of added water contributes to the degradation of amlodipine composition in liquid form. Given the fact that the liquid formulations exhibit any long term stability is surprising in view of the fact that Noburu plainly states that amlodipine besylate is incompatible with glycerin.

Effect of Antioxidant Concentration on Liquid Solution of Amlodipine

Experiments were carried out to evaluate the effect of antioxidant amount on the stability of the liquid solution of amlodipine. Three batches were prepared with differing amounts of BHA and with no added BHA, as shown in Table 5.

TABLE 5

Compositional makeup of Formulations E-H

| | Formulation ID: | | | |
| --- | --- | --- | --- | --- |
| | Form. E | Form. F | Form. G | Form. H |
| | Batch size: | | | |
| | 1 L | 1 L | 1 L | 4 L |
| | Quantity | Quantity | Quantity | Quantity |
| Ingredients | (mg)/mL | (mg)/mL | (mg)/mL | (mg)/mL |
| Amlodipine Besylate | 1.385† | 1.385† | 1.385† | 1.385† |
| Liquid Maltitol | 140.0 | — | 140.0 | 140.0 |
| BHA | — | 0.10 | 0.20 | 0.40 |
| Ethanol absolute* | 31.6‡ | — | 31.6‡ | — |
| Frozen peppermint flavor | 0.10 | 0.10 | 0.10 | 0.10 |
| Glycerin | Qs to 1 mL | — | Qs to 1 mL | — |

Abbreviation: BHA (butylated hydroxyanisole)
†Equivalent to about 1 mg/mL amlodipine.
‡Corresponds to about 0.04 mL based on ethanol density of 0.790 g/mL.
*Formulation density of about 1.25 g/mL.

An exemplary process for preparing batches of Formulations E, F, G, and H containing the above-mentioned ingredients is as follows.

1. Tare weight of SS manufacturing vessel S1: Add 98% of total batch size of glycerin SS manufacturing vessel S1.

2. Tare weight of SS manufacturing vessel S2: Add dispensed quantity of ethanol absolute from total batch size in SS manufacturing vessel S2.

3. Where appropriate, add dispensed quantity of butylated hydroxyanisole in manufacturing vessel S2 step 2, stir well until clear solution is obtained.

4. Add dispensed quantity of amlodipine besylate in manufacturing vessel S2 step 3, stir well until hazy dispersion is obtained.

5. Add 2.0% of total batch size of glycerin in manufacturing vessel S2, stir well until clear solution is obtained.

6. Transfer the content of SS manufacturing vessel S2 of step 5, to vessel S1 of step 1. Stir well until clear homogeneous solution is obtained.

7. Add dispensed quantity of Lycasin 80/55 in manufacturing vessel S1 step 6, stir well until clear solution is obtained.

8. Add dispensed quantity of frozen peppermint flavor in manufacturing vessel S1 step 7, stir well until clear solution is obtained.

9. Add remaining quantity of glycerin to make up the volume and stirred by overhead stirrer in SS manufacturing vessel S1.

10. Filter the solution using 40μ PP filter and filled in 150 mL Amber glass bottle with 28 mm CR cap.

Bottled formulations E-H were stored at 40±2° C. and 60%±5% RH for 3 months and results for Impurity A are presented in Table 6.

TABLE 6

Stability Results of Formulations E-H

| | | Form. E (no BHA) | | Form. F (0.1 mg/mL BHA) | | Form G (0.2 mg/mL BHA) | | Form. H (0.4 mg/mL BHA) | |
| --- | --- | --- | --- | --- | --- | --- | --- | --- | --- |
| | Parameters | Initial | 3 M | Initial | 3 M | Initial | 3 M | Initial | 3 M |
| | Impurity A | ND | 0.55 | ND | 0.39 | ND | 0.37 | 0.22 | 0.26 |

As per the results presented in Table 6, the following observations were noted:
(1) Impurity A increased to 0.55% after 3 months in Form. E (without BHA).
(2) Impurity A increased to 0.39% after 3 months in Form F (0.1 mg/mL BHA).
(3) Impurity A increased to 0.37% after 3 months in Form G (0.2 mg/mL BHA).
(4) Impurity-A increased to only 0.26% after 3 months from its initial level of 0.22% in Form H (0.4 mg/mL BHA).

Effect of Co-Solvent Concentration on Liquid Solution of Amlodipine with BHA as Antioxidant Experiments were carried out to evaluate the effect of concentration of co-solvent on the stability of the liquid solution of amlodipine. Three batches were prepared with different concentration of ethanol (2%, 3%, and 4%) as summarized in Table 7.

TABLE 7

Compositional makeup of Formulations I-K.

| Ingredients | Form. I Quantity (mg)/mL | Form. J Quantity (mg)/mL | Form. K Quantity (mg)/mL |
|---|---|---|---|
| | Batch size: | | |
| | 2 L | 2 L | 2 L |
| Amlodipine Besylate† | 2.77 mg | 2.77 mg | 2.77 mg |
| Liquid Maltitol | 140.0 | 140.0 | 140.0 |
| BHA | 0.40 | 0.40 | 0.40 |
| Ethanol absolute | 15.8 mg (0.02 mL/mL* or 2% v/v) | 23.7 mg (0.03 mL/mL* or 3% v/v) | 31.6 mg (0.04 mL/mL* or 4% v/v) |
| Frozen peppermint flavor | 0.1 | 0.1 | 0.1 |
| Glycerin | Qs to 1 mL | Qs to 1 mL | Qs to 1 mL |

†Equivalent to about 2 mg/mL amlodipine.
*Based on ethanol density of 0.790 g/mL.
Formulation density: 1.25 g/mL.

An exemplary process for preparing batches of Formulations I-K containing the above-mentioned ingredients is as follows.

1. Tare weight of SS manufacturing vessel S1: Add 98% of total batch size of glycerin in SS manufacturing vessel S1.
2. Tare weight of SS manufacturing vessel S2: Add specified quantity of ethanol absolute in SS manufacturing vessel S2.
3. Add dispensed quantity of butylated hydroxyanisole in manufacturing vessel S2 step 2, stir well until clear solution is obtained.
4. Add dispensed quantity of amlodipine besylate in manufacturing vessel S2 step 3, stir well until hazy dispersion is obtained.
5. Add 2% of total batch size of glycerin in manufacturing vessel S2, stir well until clear solution is obtained.
6. Transfer the content of SS manufacturing vessel S2 of step 5, to vessel S1 of step 1. Stir well until clear homogeneous solution is obtained.
7. Add dispensed quantity of Lycasin 80/55 in manufacturing vessel S1 step 6, stir well until clear solution is obtained.
8. Add dispensed quantity of frozen peppermint flavor in manufacturing vessel S1 step 7, stir well until clear solution is obtained.
9. Add remaining quantity of glycerin to make up the volume 2 L(=2.5 kg) and stirred by overhead stirrer in SS manufacturing vessel S1
10. Filter the solution using 40 μm PP filter and filled in 150 mL Amber glass bottle with 28 mm CR cap.

Observations with Respect to Formulations I-K.

The batches prepared as per above composition were observed during preparation as well as after preparation.

As related to Formulation I, (2% v/v volume ethanol), amlodipine did not dissolve completely (more than 50%), and also at the end of batch more than 20% amlodipine remain undissolved.

As related to Formulation J (3% v/v volume of ethanol), amlodipine did not dissolve completely (more than 20-30%) and at the end of batch it took very long time to get amlodipine dissolved.

As related to Formulation K (4% v/v volume of ethanol), amlodipine dissolved completely during process and remain dissolved after preparation and during observation for some time.

Preparation of Formulation L

TABLE 8

Compositional makeup of Formulation L

| Formulation ID: | Formulation L | |
|---|---|---|
| Batch Size | 5 L | 6.25 kg |
| Ingredients | Quantity (mg/mL) | Quantity (g/batch) |
| Amlodipine besylate† | 1.385 | 6.925 |
| Maltitol (Liquid) | 140.0 | 700.0 |
| Butylhydroxyanisole | 0.40 | 2.00 |
| Ethanol, Absolute | 31.6 mg (0.04 mL/mL*) | 158 |
| Frozen Peppermint Flavor | 0.1 | 0.5 |
| Glycerin | Qs to 1 mL | Qs to 5 L |

†Equivalent to about 1 mg/mL amlodipine.
*Based on ethanol density of 0.790 g/mL.
Formulation density: 1.25 g/mL.

Batch Manufacturing Procedure for Formulation L.

1. Tare weight of SS manufacturing Vessel S1: Add 98% of total batch size of glycerin SS manufacturing Vessel S1.
2. Tare weight of SS manufacturing Vessel S2: Add dispensed quantity of ethanol absolute from total batch size in SS manufacturing Vessel S2.
3. Add dispensed quantity of butylated hydroxyanisole in manufacturing Vessel S2 step 2, stir well until clear solution is obtained.
4. Add dispensed quantity of amlodipine besylate in manufacturing Vessel S2 step 3, stir well until hazy dispersion is obtained.
5. Add 2.0% of total batch size of glycerin in manufacturing Vessel S2, stir well until clear solution is obtained.
6. Transfer the content of SS manufacturing Vessel S2 of step 5, to Vessel S1 of step 1. Stir well until clear homogeneous solution is obtained.
7. Add dispensed quantity of Lycasin 80/55 in manufacturing Vessel S1 step 6, stir well until clear solution is obtained.
8. Add dispensed quantity of frozen peppermint flavor in manufacturing Vessel S1 step 7, stir well until clear solution is obtained.
9. Add remaining quantity of glycerin to make up the volume and stirred by overhead stirrer in SS manufacturing Vessel S1.
10. Filter the solution using 40μ PP filter and filled in 150 mL amber glass bottle with 28 mm CR cap.

Bottled samples of Formulation L were stored at 40±2° C. and 75±5% RH and 25±2° C. and 60%±5% RH for 3 months and 6 months. Table 9 reports observations related to Description, AB Assay (by HPLC), BHA Assay (by HPLC), and Ethanol Assay (by GC) with respect to labeled content, as well as the observed values for Impurity A, Single maximum unknown impurity ("SMUI"), and Total Impurities ("Tot. Imps.").

TABLE 9

Stability Results of Formulation L

| Parameters | Specifications | Initial | 40° C./ 75% RH 3M | 25° C./60% RH 3M | 40° C./75% RH 6M | 25° C./60% RH 6M |
|---|---|---|---|---|---|---|
| Description | A clear pale straw colored, viscous liquid. | Complies | Complies | Complies | Complies | Complies |
| AB Assay | Between 90% and 110% of 1.358 mg/mL | 99.7% | 98.2% | 100.6% | 94.6% | 98.0% |
| BHA Assay | Between 70% and 110% of 0.40 mg/mL | 98.5% | 95.7% | 99.3% | 90.4% | 93.3% |
| Ethanol Assay | Between 70% and 110% of 31.6 mg/mL | 91.1% | 92.6% | 94.6% | 94.0% | 96.3% |
| Organic impurities (By HPLC) | | | | | | |
| Impurity A | NMT 3.0% | 0.22% | 0.75% | 0.26% | 2.17% | 0.63% |
| SMUI | NMT 0.2% | 0.04% | 0.13% | 0.04% | 0.21% | BQL |
| Tot. Imps. | NMT 3.5% | 0.32% | 1.09% | 0.31% | 2.71% | 0.63% |

Amlodipine Oral Solution showed no significant change in physico-chemical parameters during stability studies at 25±2° C./60±5% RH up to 6 months.

Preparation of Formulation M

TABLE 10

Compositional makeup of Formulation M

| Formulation ID: | Form. M | |
|---|---|---|
| Batch size | 180 L | 180 L/225 kg |
| Ingredients | Quantity (mg)/mL | Quantity per batch |
| Amlodipine Besylate† | 1.385 mg | 250.20 g |
| Liquid Maltitol | 140.0 | 25.20 kg |
| BHA | 0.40 | 72.00 g |
| Ethanol absolute | 31.6* | 5.69 kg |
| Frozen peppermint flavor | 0.10 | 18.00 g |
| Glycerin | ≈1076.5‡ Qs to 1 mL | 193.77 kg |

†Equivalent to about 1 mg/mL amlodipine.
*Based on ethanol density of 0.790 g/mL.
‡Based on target density: 1.25 g/mL.

1. Tare weight of SS manufacturing vessel S1: Add about 91% of total batch size of glycerin in SS manufacturing vessel S1; mix liquid at about 10 Hz under a vacuum of about 0.35 bar for about 10 minutes.

2. Tare weight of SS manufacturing vessel S2: Add specified quantity of Ethanol absolute in SS manufacturing vessel S2.

3. Add dispensed quantity of butylated hydroxyanisole in manufacturing vessel S2 step 2, stir for about 10 to about 15 min at about 30 Hz until clear solution is obtained.

4. Add dispensed quantity of amlodipine besylate in manufacturing vessel S2 step 3, stir for about 10 to about 15 min at 30 Hz until hazy dispersion is obtained.

5. Add about 2% of total batch size of glycerin in manufacturing vessel S2, stir for about 15 to about 25 min at 30 Hz.

6. If necessary, add a compensatory amount of ethanol to S2 while stirring for about 1 to about 2 min at 30 Hz.

7. Transfer the content of SS manufacturing vessel S2 of step 5 (or step 6), to vessel S1 of step 1. Stir well until clear homogeneous solution is obtained.

8. Add about 2% of total batch size of glycerin in manufacturing vessel S2 (rinsing) while stirring at about 5 min to about 10 min at 40 Hz; and then transfer contents of S2 to S1.

9. Add dispensed quantity of liquid maltitol (e.g., Lycasin 80/55) in manufacturing vessel S1 step 8, stir for about 30 min to about 35 min at 10 Hz.

10. Add dispensed quantity of frozen peppermint flavor in manufacturing vessel S1 step 9, stir at about 10 min to about 15 min at 15 Hz.

11. Add remaining quantity of glycerin to make up the volume 180 L=250 kg and stirred by overhead stirrer from about 80 min to about 90 min at 15 Hz.

10. Filter the solution using 40 μm PP filter and filled in 150 mL Amber glass bottle with 28 mm CRC/PP Cap, TE EPE lined.

Based on experience and literature support, amber-PET and amber-glass material was selected for Amlodipine Oral Solution, which was readily used in other approve marketed products and common for oral solutions. Comparative stability data at accelerated conditions of Amlodipine Oral Solution stored in amber PET and amber glass bottle.

Based on data obtained during development, it was observed that a formulation described herein filled in Amber PET bottle with induction seal (e.g., PP 28 child resistant closure with an IHS safe-guard 605 liner-induction seal) showed a higher percent of Impurity A as compared to product filled in amber glass bottle (see DMF No. 14003) with a pharmaceutically acceptable closure (such as a 28 mm Polypropylene TE-CRC cap with EPE liner, see DMF No. 18371). Impurity A in Amber PET bottle was found at a level of 1.05% when stored at 40° C./NMT 25% RH for 3 months. Whereas, Impurity A in amber glass bottle was found to be 0.58%, 40° C./75% RH after 3 months. Though both results meet specifications, amber, glass bottles are selected as a viable commercial packaging and will be used moving forward.

Bottled samples of three separate batches of Formulation M were stored at 40±2° C. and 75±5% RH for 6-months, 30±2° C./65±5% RH for 12-months, and 25±2° C. and 60%±5% RH for 18-months. Tables 11-13 report observations for a single batch (e.g., Formulation M, 180 L) related to AB Assay (by HPLC), BHA Assay (by HPLC), and Ethanol Assay (by GC) with respect to labeled content, as well as the observed values for Impurity A, Single maximum unknown impurity ("SMUI"), and Total Impurities ("Tot. Imps."). In instances where the observed substance (or impurity) is lower than the detection limit, reference is made to the acronym BLOQ Tests (not shown) relate to density (specification of 1.23 to 1.28 g/mL with an observed value of 1.254±0.002 g/mL) and description (a clear pale straw colored, viscous liquid (all time points comply). The batch complied with these additional tests when stored at 25±2° C. and 60%±5% RH either upright or inverted.

Bioequivalence Study

Pilot bioequivalence studies were performed comparing a formulation (viz., a representative batch of Formulation M, supra) with NORVASC® (amlodipine besylate) 10 mg tablets. A summary of the bioequivalence studies are provided below.

TABLE 11

Stability Results of Representative Batch of Formulation M at 40 ± 2° C. and 75 ± 5% RH

| Test | Specs. | 1 M (I) | 2 M (I) | 3 M (I) | 3 M (U) | 6 M (I) | 6 M (U) |
|---|---|---|---|---|---|---|---|
| AB Assay | 100 ± 10% L.C. | 100.0 | 99.3 | 99.1 | 99.4 | 98.6 | 98.7 |
| BHA Assay | NLT 70%; NMT 110% | 99.2 | 98.6 | 97.0 | 98.6 | 96.5 | 98.5 |
| EtOH Assay | NLT 70%; NMT 110% | 101.2 | 101.8 | 96.9 | 96.9 | 98.2 | 97.7 |
| Impurity A | NMT 3% | 0.23 | 0.38 | 0.52 | 0.28 | 0.75 | 0.35 |
| SMUI | NMT 0.2% | 0.06 | BLOQ | 0.10 | 0.08 | 0.17 | 0.17 |
| Tot. Imp. | NMT 3.5% | 0.29 | 0.38 | 0.77 | 0.50 | 0.99 | 0.61 |

Tests (not shown) relate to density (specification of 1.23 to 1.28 g/mL with an observed value of 1.255±0.002 g/mL) and description (a clear pale straw colored, viscous liquid (all time points comply). The batch complied with these additional tests when stored at 40±2° C. and 75±5% RH either upright or inverted.

Test Product: Amlodipine (1 mg/mL) Formulation
Listed Drug: NORVASC® (amlodipine besylate) 10 mg Tablets Pfizer Labs, Division of Pfizer Inc, NY, NY 10017

Bioequivalence studies were undertaken in fasting adults (N=32). Pharmacokinetic parameters were derived individually for each analyzed subject from the plasma concentra-

TABLE 12

Stability Results of Representative Batch of Formulation M at 30 ± 2° C./65 ± 5% RH The specifications are the same as those identified in Table 11.

| Test | 3 M (I) | 3 M (U) | 6 M (I) | 6 M (U) | 9 M (I) | 12 M (I) | 12 M (U) |
|---|---|---|---|---|---|---|---|
| AB Assay | 100.7 | 100.0 | 100.6 | 99.8 | 99.6 | 98.5 | 98.7 |
| BHA Assay | 99.3 | 99.4 | 98.3 | 98.4 | 98.4 | 95.8 | 96.3 |
| EtOH Assay | 97.9 | 96.8 | 98.1 | 96.8 | 101.9 | 99.6 | 98.5 |
| Impurity A | 0.20 | 0.19 | 0.37 | 0.29 | 0.55 | 0.81 | 0.60 |
| SMUI | 0.08 | 0.07 | BLOQ | BLOQ | 0.09 | 0.09 | 0.09 |
| Tot. Imp. | 0.34 | 0.26 | 0.37 | 0.29 | 0.85 | 0.90 | 0.70 |

Tests (not shown) relate to density (specification of 1.23 to 1.28 g/mL with an observed value of 1.255±0.003 g/mL) and description (a clear pale straw colored, viscous liquid (all time points comply). The batch complied with these additional tests when stored at 30±2° C./65±5% RH either upright or inverted.

tion-time profiles of amlodipine. Actual time of blood sample collection was used for the estimation of pharmacokinetic parameters. The mean pharmacokinetic parameters of Amlodipine Oral Solution as the test product (T) and NORVASC® Tablets as the reference product (R) have been summarized below in Table 14 and Table 15.

TABLE 13

Stability Results of Representative Batch of Formulation M at 25 ± 2° C and 60% ± 5% RH The specifications are the same as those identified in Table 11.

| Test | 3 M (I) | 3 M (U) | 6 M (I) | 6 M (U) | 9 M (I) | 12 M (I) | 12 M (U) | 18 M (I) | 18 M (U) |
|---|---|---|---|---|---|---|---|---|---|
| AB Assay | 100.4 | 100.6 | 99.4 | 99.5 | 100.0 | 100.0 | 99.6 | 99.2 | 99.4 |
| BHA Assay | 99.6 | 100.0 | 99.0 | 98.7 | 99.8 | 97.6 | 97.5 | 96.6 | 97.4 |
| EtOH Assay | 99.1 | 100.1 | 98.1 | 98.0 | 102.8 | 100.2 | 98.7 | 101.8 | 103.4 |
| Impurity A | 0.12 | 0.12 | 0.26 | 0.23 | 0.35 | 0.48 | 0.42 | 0.67 | 0.47 |
| SMUI | 0.08 | 0.09 | 0.06 | BLOQ | 0.06 | BLOQ | BLOQ | BLOQ | BLOQ |
| Tot. Imp. | 0.27 | 0.28 | 0.32 | 0.23 | 0.41 | 0.48 | 0.42 | 0.67 | 0.47 |

TABLE 14

Descriptive Statistics of Formulation Means for Amlodipine Obtained by a Non-Compartmental Model (N = 32)

| Pharmacokinetic Parameters (Units) | Mean ± SD (Un-transformed data) | |
|---|---|---|
| | Test Product (T) | Reference Product (R) |
| Cmax (ng/mL) | 8.7619 ± 1.84919 | 8.3962 ± 1.79634 |
| AUC0-72 h (ng.hr/mL) | 343.2637 ± 71.36683 | 325.6716 ± 62.47180 |
| Kel (hr−1) | 0.0141 ± 0.00336 | 0.0144 ± 0.00316 |
| t1/2 (hr) | 52.3110 ± 14.64684 | 50.3930 ± 10.56366 |
| Tmax (hr) | 6.469 ± 1.6798 | 6.172 ± 1.3947 |
| | Median | |
| Tmax (hr) | 6.000 | 6.000 |

TABLE 15

Geometric Least Squares Means, Ratios and 90% Confidence Intervals for Pharmacokinetic Parameters (Cmax and AUC0-72 h) of Amlodipine (N = 33) (Including Outliers)

| Pharmacokinetic Parameters (Units) | Ln-transformed Geometric Least Squares Mean | | | 90% Confidence Interval (Parametric) | |
|---|---|---|---|---|---|
| | Test Product (T) | Reference Product (R) | T/R (%) | Lower | Upper |
| Cmax (ng/mL) | 8.5697 | 8.2147 | 104.32 | 99.20 | 109.71 |
| AUC0-72 h (ng.hr/mL) | 336.0381 | 319.9374 | 105.03 | 100.95 | 109.28 |

The 90% confidence intervals of the differences of least squares means for the Ln-transformed pharmacokinetic parameters Cmax and AUC0-72 h of amlodipine are within the bioequivalence acceptance limits of 80.00-125.00%.

In view of the foregoing information, it is concluded that the test product (T), was found to be bioequivalent with reference product (R) NORVASC® (amlodipine) 10 mg Tablets of Pfizer Labs NY 10017 in healthy, adult, human subjects under fasting conditions.

A second study examined the food effect on the pharmacokinetic parameters for the test product, Amlodipine Oral Solution. Subjects (N=31) were giving Amlodipine Oral Solution fasted and after a high-fat, high-calorie, non-vegetarian breakfast. Samples and statistical analysis was handled in a similar fashion as the fasting study. A summary of the results from the food effect study is listed in Table 16 and Table 17.

TABLE 16

Descriptive Statistics of Formulation Means for Amlodipine Obtained by a Non-Compartmental Model (N =31)

| Pharmacokinetic Parameters (Units) | Mean ± SD (Un-transformed data) | |
|---|---|---|
| | Test Product (Tfed) | Test Product (Tfast) |
| Cmax (ng/mL) | 8.5176 ± 1.58377 | 8.7179 ± 1.39330 |
| AUC0-72 h (ng.hr/mL) | 348.9069 ± 63.16044 | 345.1714 ± 63.17824 |
| Tmax (hr) | 6.550 ± 2.1351 | 7.290 ± 2.1709 |
| | Median | |
| Tmax (hr) | 6.000 | 7.500 |

TABLE 17

Geometric Least Squares Means, Ratios and 90% Confidence Intervals for Pharmacokinetic Parameters (Cmax and AUC0-72 h) of Amlodipine (N = 31) (Including Outliers)

| Pharmacokinetic Parameters (Units) | Ln-transformed Geometric Least Squares Mean | | | 90% Confidence Interval (Parametric) | |
|---|---|---|---|---|---|
| | Test Product (Tfed) | Test Product (Tfast) | Tfed/ Tfast (%) | Lower | Upper |
| Cmax (ng/mL) | 8.3748 | 8.6192 | 97.16 | 93.13 | 101.38 |
| AUC0-72 h (ng.hr/mL) | 343.2017 | 339.7738 | 101.01 | 97.02 | 105.16 |

The 90% confidence intervals of the differences of least squares means for the Ln-transformed pharmacokinetic parameters Cmax and AUC0-72 h of amlodipine are within the acceptance limits of 80.00-125.00%.

In view of the foregoing information, it is concluded that there is no food effect observed for the test (T) product (Dose: 10 mL equivalent to the dose of 10 mg of amlodipine) in healthy, adult, human subjects under fed versus fasting conditions. These clinical results are consistent with the dissolution results of amlodipine in FaSSIF and FeSSIF dissolution media (not shown).

Additional Formulations

Formulations without added ethanol were evaluated for further consideration. Table 18 summarizes the compositional makeup of three formulations without ethanol (Formulations N-P).

TABLE 18

Compositional makeup of Formulations N-P

| Formulation ID: | Form. N | | Form. O | | Form. P | |
|---|---|---|---|---|---|---|
| Ingredients | Amount (g) | % w/w | Amount (g) | % w/w | Amount (g) | % w/w |
| Amlodipine Besylate | 0.277 | 0.136 | 0.277 | 0.112 | 0.277 | 0.127 |
| MagnaSweet | — | — | — | — | 0.400 | 0.183 |
| Liquid Maltitol | — | — | 28 | 11.360 | — | — |
| BHA | 0.080 | 0.039 | 0.080 | 0.032 | 0.080 | 0.037 |
| Propylene Glycol | 14.3 | 7.004 | 28.6 | 11.604 | 28.6 | 13.067 |
| Mixed Berry Flavor | 0.020 | 0.010 | 0.020 | 0.008 | 0.020 | 0.009 |
| Glycerin | 189.5 | 92.812 | 189.5 | 76.883 | 189.5 | 86.578 |
| Δ Assay (%) | 8.0 | | 8.7 | | 11.3 | |
| Tot. Imps. (%) | 2.1 | | 2.7 | | 2.8 | |

A preliminary (i.e., non-validated) study was performed by storing samples of Formulations N-P for 6-weeks at 60° C. and by evaluating the samples for amlodipine besylate assay and total impurities.

The results of the study showed that amlodipine besylate assay after 6-weeks ("A Assay") was reduced by only about 8% for Formulation N, while amlodipine besylate assay was reduced by about 11.3% for Formulation P.

The results of the study also showed that the amount of total impurities ("Tot. Imps.") increased by about 2.1% for Formulation N, while total impurities increased by about 2.8% for Formulation P.

The results observed for Formulation N (with no added water) showed that an amlodipine besylate formulation substantially free of water (viz., having a water content of about 0.01% w/w or lower) showed improved stability compared to other formulations (e.g., Formulation P) containing water.

One will appreciate the Arrhenius kinetic model states that generally for every 10° C. change in temperature, then the degradation rate changes by a factor of two. That said, and working under the assumption that amlodipine degradation follows an Arrhenius kinetic model, it is estimated that Formulation N has shelf-life of at least about 17 months, while Formulation 0 has a shelf-life of at least about 20-months when samples are stored at 25±2° C. and 60%±5% RH. Additional data may support a specification of 100±10% labeled claim stability for at least 24-months when bottled samples are stored at 25±2° C. and 60%±5% RH.

Practical Utility

The formulations disclosed herein show practical utility with respect to long-term stability and content uniformity.

The liquid formulations disclosed herein exhibit improved properties compared to the commercially marketed KATERZIA® suspension product because there is no need to refrigerate to maintain a suitable shelf-life of up to 24-months. Additionally, there would be no concern with respect to content uniformity for the liquid formulations disclosed herein compared to the KATERZIA® suspension product.

The formulations disclosed herein are superior to the Mandal formulations, which included added water of about 11% w/w, and showed reduced amlodipine stability.

The liquid pharmaceutical formulation substantially free of water (and/or ethanol), comprising: (i) 100±10% labeled content when stored for about 24-months at 25±2° C. and 60±5% relative humidity; (ii) 100±10% labeled content when stored for about 18-months at 25±2° C. and 60±5% relative humidity; (iii) 100±10% labeled content when stored for about 12-months at 25±2° C. and 60±5% relative humidity; (iv) 100±5% labeled content when stored for about 24-months at 25±2° C. and 60±5% relative humidity; (v) 100±5% labeled content when stored for about 18-months at 25±2° C. and 60±5% relative humidity; (vi) 100±5% labeled content when stored for about 12-months at 25±2° C. and 60±5% relative humidity; (vi) 100±5% labeled content when stored for about 12-months at 30±2° C. and 65±5% relative humidity; and/or (vii) 100±5% labeled content when stored for about 6-months at 40±2° C. and 75±5% relative humidity. These findings are particularly surprising considering that Noburu plainly states that amlodipine besylate is incompatible with glycerin.

Based on a review of the exemplified embodiments disclosed herein, one may appreciate that a formulation disclosed herein does not contain a surfactant. Thus, contemplated herein is a liquid pharmaceutical formulation substantially free of water (and/or ethanol), that contains no surfactant.

One may appreciate that the expression "comprising" may be replaced with the expression "consisting of" to reflect a formulation disclosed herein.

CITED INFORMATION

Berge et al., *Pharmaceutical Salts*, J. Pharm. Science (1977) 66(1): 1-19 ("Berge").

Handbook of Pharmaceutical Excipients, Sixth Edition (2009), Rowe et al. Eds. ("Handbook").

JP 2009-256216 A, *Liquid amlodipine besylate formulation for internal administration stable in solution state*, to Noboru et al. of Towa Yakuhin KK ("Noburu").

KATERZIA® (amlodipine) oral suspension, for oral use, prescribing information as of Jul. 8, 2019 ("KATERZIA® Label").

Murakami et al., *Application of liquid chromatography-two-dimensional nuclear magnetic resonance spectroscopy using pre-concentration column trapping and liquid chromatography-mass spectrometry for the identification of degradation products in stressed commercial amlodipine maleate tablets*, J. Chromatog. A (2008) 1181(1-2): 67-76 ("Murakami").

Nahata et al., *Stability of Amlodipine Besylate in Two Liquid Dosage Forms*, J. Am. Pharm. Assoc. (1999) 39: 375-377 ("Nahata").

NORVASC® (amlodipine besylate) tablets for oral administration prescribing information, as of Oct. 30, 2017 ("NORVASC® Label").

Ragno et al., *Photodegradation monitoring of amlodipine by derivative spectrophotometry*, J. Pharm. Biomed. Anal. (2002) 27(1): 19-24 ("Ragno").

Rapolu et al., *Isolation and characterization of a novel acid degradation impurity of Amlodipine Besylate using Q-TOF, NMR, IR and single crystal X-ray*, J. Pharm. Biomed. Anal. (2014) 99: 59-66 ("Rapolu").

Stopher et al., *The Metabolism and Pharmacokinetics of Amlodipine in Humans and Animals*, J. Cardiovasc Pharmacol. (1988) 12(Suppl. 7): S55-S59 ("Stopher").

UK Patent Application GB 2 166 637 A, Drink Concentrate, to Leslie William David of Powell & Scholefield Limited ("Dodd").

U.S. Pat. No. 4,879,303, *Pharmaceutically Acceptable Salts*, to Davison et al. of Pfizer ("Davison").

U.S. Pat. No. 7,108,885, *Liquid Maltitol Composition, Process for its Manufacture and its Uses*, to Michel Serpelloni of Roquette Freres ("Serpelloni").

U.S. Pat. No. 10,695,329, Amlodipine Formulations, to Brauer et al. of Silvergate Pharmaceuticals, Inc. ("Brauer").

U.S. Patent Application Publication No. 2011/0294860 A1, *Aqueous Oral Preparation of Stable Amlodipine*, to Tatsumi et al. of MedRx Co. Ltd. ("Tatsumi").

U.S. Patent Application Publication No. 2018/0303811 A1, *Oral Solution of Dihydropyridine Derivatives*, Mandal et al., of FTF Pharma Private Limited ("Mandal").

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

As stated above, this application claims priority to U.S. Provisional Patent Application No. 63/144,021, filed on Feb. 1, 2021, the entire subject matter of which is incorporated by reference.

The references and documents described herein are incorporated by reference in their entirety to the extent necessary. If there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

The invention claimed is:

1. An oral liquid pharmaceutical formulation, comprising:
   from about 0.08% w/w to about 0.18% w/w of amlodipine besylate,
   at least one pharmaceutically acceptable excipient, and
   a vehicle comprising from about 80% w/w to about 96% w/w glycerin;
   wherein the oral liquid pharmaceutical formulation has a water content of less than or equal to about 5% w/w.

2. The oral liquid formulation of claim 1, wherein the amount of amlodipine besylate is present in an amount of from about 0.10% w/w to about 0.16% w/w.

3. The oral liquid formulation of claim 1, wherein the amount of amlodipine besylate is present in an amount of from about 0.10% w/w to about 0.14% w/w.

4. The oral liquid formulation of claim 1, wherein the amount of amlodipine besylate is present in an amount of from about 0.10% w/w to about 0.12% w/w.

5. The oral liquid formulation of claim 1, wherein the amount of amlodipine besylate is present in an amount of about 0.11% w/w.

6. The oral liquid formulation of claim 1, wherein the vehicle comprises about 82% w/w to about 94% w/w glycerin.

7. The oral liquid formulation of claim 1, wherein the vehicle comprises about 84% w/w to about 92% w/w glycerin.

8. The oral liquid formulation of claim 1, wherein the vehicle comprises about 84% w/w to about 90% w/w glycerin.

9. The oral liquid formulation of claim 1, wherein the at least one pharmaceutically acceptable excipient comprises a sweetener agent, an antioxidant, a co-solvent, a flavoring agent, or a combination thereof.

10. The oral liquid formulation of claim 1, wherein the at least one pharmaceutically acceptable excipient comprises a sweetener agent in an amount of from about 0.1% w/w to about 11% w/w.

11. The oral liquid formulation of claim 1, wherein the at least one pharmaceutically acceptable excipient comprises a sweetener agent in an amount of from about 4% w/w to about 11% w/w.

12. The oral liquid formulation of claim 1, wherein the at least one pharmaceutically acceptable excipient comprises a sweetener agent in an amount of from about 8% w/w to about 11% w/w.

13. The oral liquid formulation of claim 1, wherein the at least one pharmaceutically acceptable excipient comprises a sweetener agent comprising maltitol in an amount of from about 5.5% w/w to about 7.0% w/w.

14. The oral liquid formulation of claim 1, wherein the at least one pharmaceutically acceptable excipient comprises a sweetener agent comprising maltitol in an amount of from about 5.6% w/w to about 6.6% w/w.

15. The oral liquid formulation of claim 1, wherein the at least one pharmaceutically acceptable excipient comprises a sweetener agent comprising maltitol in an amount of from about 5.6% w/w to about 6.0% w/w.

16. The oral liquid formulation of claim 1, wherein the at least one pharmaceutically acceptable excipient comprises an antioxidant in an amount of from about 0.01% w/w to about 0.09% w/w.

17. The oral liquid formulation of claim 1, wherein the at least one pharmaceutically acceptable excipient comprises an antioxidant in an amount of from about 0.01% w/w to about 0.07% w/w.

18. The oral liquid formulation of claim 1, wherein the at least one pharmaceutically acceptable excipient comprises an antioxidant in an amount of from about 0.01% w/w to about 0.05% w/w.

19. The oral liquid formulation of claim 1, wherein the at least one pharmaceutically acceptable excipient comprises a co-solvent in an amount of from about 1% w/w to about 15% w/w.

20. The oral liquid formulation of claim 1, wherein the at least one pharmaceutically acceptable excipient comprises a co-solvent in an amount of from about 1% w/w to about 10% w/w.

21. The oral liquid formulation of claim 1, wherein the at least one pharmaceutically acceptable excipient comprises a co-solvent in an amount of from about 1% w/w to about 8% w/w.

22. The oral liquid formulation of claim 1, wherein the at least one pharmaceutically acceptable excipient comprises a co-solvent in an amount of from about 1% w/w to about 5% w/w.

23. A container comprising written material and a bottle comprising the oral liquid formulation of claim 1.

24. A container comprising written material and a bottle comprising the oral liquid formulation of claim 5.

25. The oral liquid formulation of claim 1, wherein the liquid pharmaceutical formulation has a water content of less than or equal to about 3% w/w.

26. A method for the treatment of a condition, which comprises administering to a patient in need thereof a therapeutically effective amount of the oral liquid formulation of claim 1; wherein the condition is treatment of hypertension, the symptomatic treatment of chronic stable angina, the treatment of vasospastic angina, or the treatment of a coronary artery disease; and wherein the patient is an adult patient or a pediatric patient.

27. A method for the treatment of a condition, which comprises administering to a patient in need thereof a therapeutically effective amount of the oral liquid formulation of claim 1, wherein the condition is treatment of hypertension; and wherein the patient is an adult patient or a pediatric patient.

28. A method for the treatment of a condition, which comprises administering to a patient in need thereof a therapeutically effective amount of the oral liquid formulation of claim 1; wherein the condition is the symptomatic treatment of chronic stable angina; and wherein the patient is an adult patient or a pediatric patient.

29. A method for the treatment of a condition, which comprises administering to a patient in need thereof a therapeutically effective amount of the oral liquid formulation of claim 1; wherein the condition is the treatment of vasospastic angina; and wherein the patient is an adult patient or a pediatric patient.

30. A method for the treatment of a condition, which comprises administering to a patient in need thereof a therapeutically effective amount of the oral liquid formulation of claim 1; wherein the condition is treatment of a coronary artery disease; and wherein the patient is an adult patient or a pediatric patient.

* * * * *